(12) United States Patent
Kimura et al.

(10) Patent No.: US 8,304,538 B2
(45) Date of Patent: Nov. 6, 2012

(54) METHOD OF PRODUCING BENZOXAZINONE-BASED COMPOUND

(75) Inventors: Keizo Kimura, Odawara (JP); Takashi Kitagawa, Odawara (JP); Osamu Uchida, Odawara (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 265 days.

(21) Appl. No.: 12/680,377

(22) PCT Filed: Sep. 25, 2008

(86) PCT No.: PCT/JP2008/067879
§ 371 (c)(1),
(2), (4) Date: Mar. 26, 2010

(87) PCT Pub. No.: WO2009/041715
PCT Pub. Date: Apr. 2, 2009

(65) Prior Publication Data
US 2010/0256362 A1    Oct. 7, 2010

(30) Foreign Application Priority Data

Sep. 27, 2007  (JP) ................................. 2007-252729
Mar. 31, 2008  (JP) ................................. 2008-091834

(51) Int. Cl.
C07D 265/22    (2006.01)
C07D 413/04    (2006.01)
(52) U.S. Cl. ......................................... 544/92; 562/455
(58) Field of Classification Search .................... 544/92; 562/455
See application file for complete search history.

(56) References Cited

U.S. PATENT DOCUMENTS

| 3,408,326 | A | 10/1968 | Errede |
| 3,989,698 | A | 11/1976 | Jacobs et al. |
| 2003/0096889 | A1 | 5/2003 | Sarkar |

FOREIGN PATENT DOCUMENTS

| GB | 2 262 097 A | 6/1993 |
| JP | 58-194854 A | 11/1983 |
| JP | 61-291575 A | 12/1986 |
| JP | 62-011744 A | 1/1987 |
| JP | 62-005944 B | 2/1987 |
| JP | 62-031027 B | 7/1987 |
| JP | 2000-264879 A | 9/2000 |
| JP | 2005-507006 A | 3/2005 |
| RU | 2 161 611 C1 | 1/2001 |

OTHER PUBLICATIONS

Office Action (Notification for the Opinion of Examination) from Taiwanese Patent Office issued in corresponding Taiwanese Patent Application No. 097137087 dated Jul. 14, 2011, with an English translation.
Office Action from the State Intellectual Property Office of the People's Republic of China issued in corresponding Chinese Patent Application No. 200880109152.8 dated Jul. 20, 2011, with an English translation.
International Search Report (PCT/ISA/210) for PCT/JP2008/067879 dated Nov. 25, 2008.
Office Action from Taiwanese Patent Office issued in corresponding Taiwanese Patent Application No. 097137087 dated Jan. 5, 2012, with an English translation.

*Primary Examiner* — Kahsay T Habte
(74) *Attorney, Agent, or Firm* — Buchanan Ingersoll & Rooney PC

(57) ABSTRACT

A method of producing a compound represented by Formula (I), which comprises a step A of reacting an anthranilic acid compound with a carboxylic halide in the absence of a base, but does not comprise a step of isolating of an amide intermediate compound represented by Formula (II):

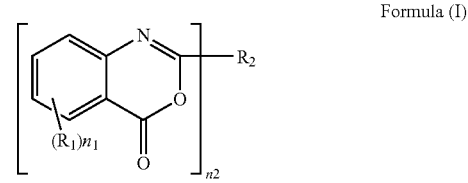

Formula (I)

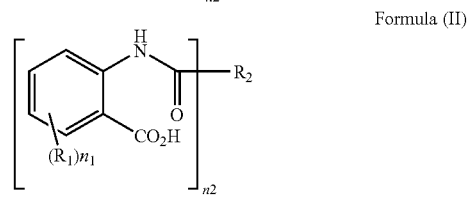

Formula (II)

wherein $R_1$ represents a substituent; $n_1$ is an integer of 0 to 4; $R_2$ represents an $n_2$-valent substituent or a linking group; and $n_2$ is an integer of 1 to 4.

7 Claims, No Drawings

METHOD OF PRODUCING BENZOXAZINONE-BASED COMPOUND

TECHNICAL FIELD

The present invention relates to a method of producing an ultraviolet absorbent for thermoplastic polymers, more specifically, to an inexpensive and effective method of producing a high-purity benzoxazinone-based compound, an ultraviolet absorbing material useful in optical film application.

BACKGROUND ART

Benzotriazole-based compounds, benzophenone-based compounds, salicylic acid-based compounds, triazine-based compounds and the like have been used as the ultraviolet absorbents for thermoplastic polymers. These ultraviolet absorbents generally had problems such as insufficient ultraviolet cut rate, insufficient heat resistance, easy color development, and insufficient fastness.

Benzoxazinone compounds have been proposed as the ultraviolet absorbents solving the problems above (see, e.g., JP-B-62-5944 ("JP-B" means examined Japanese patent publication) and JP-B-62-31027). A method of producing such a compound by using isatoic acid anhydride as the raw material is already known, but the method is still not satisfactory in that the raw material is expensive (see, e.g., U.S. Pat. No. 3,989,698 or JP-A-62-11744 ("JP-A" means unexamined published Japanese patent application)).

Also known is a method of using anthranilic acid as the raw material, but the method, which is a two-step process via an amide intermediate, was complicated in operation and lower in productivity, demanding further improvement (see, e.g., U.S. Pat. No. 3,408,326, JP-A-58-194854 and JP-A-61-291575).

Processes of producing it continuously from anthranilic acid without isolation of the amide intermediate to solve the problems above are also known (see, e.g., JP-A-2000-264879), but addition of an inorganic alkali as a base, such as sodium carbonate, for control of by-product generation in the amide intermediate-generating step caused a problem of sodium contamination in the final isolated product and deterioration in quality.

DISCLOSURE OF INVENTION

According to the present invention, there is provided the following means:

[1] A method of producing a compound represented by Formula (I), which comprises a step A of reacting an anthranilic acid compound with a carboxylic halide in the absence of a base, but does not comprise a step of isolating an amide intermediate compound represented by Formula (II):

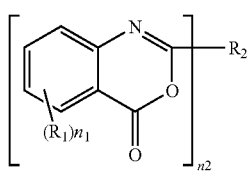

Formula (I)

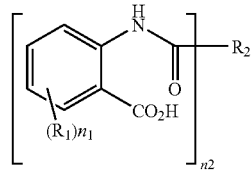

Formula (II)

wherein $R_1$ represents a substituent; $n_1$ is an integer of 0 to 4; $R_2$ represents an $n_2$-valent substituent or a linking group; and $n_2$ is an integer of 1 to 4;

[2] The method described in the above item [1], wherein at least one kind of reaction solvent used in the step A has a donor number of 10 or more;

[3] The method described in the above item [1] or [2], wherein no protic solvent is used in the step A;

[4] The method described in any one of the above items [1] to [3], wherein the temperature of the step A is 50° C. or lower; and

[5] The method described in any one of the above items [1] to [4], wherein the carboxylic halide is prepared by acid halogenation of a carboxylic acid compound and used as it is without isolation after preparation.

Other and further features and advantages of the invention will appear more fully from the following description.

BEST MODE FOR CARRYING OUT INVENTION

The present invention is explained in detail below.

In the present specification, the aliphatic group means an alkyl group, a substituted alkyl group, an alkenyl group, a substituted alkenyl group, an alkynyl group, a substituted alkynyl group, an aralkyl group, and a substituted aralkyl group. The aforementioned alkyl group may have a branch or may form a ring (i.e. a cycloalkyl group). The alkyl group preferably has 1 to 20 carbon atoms, and more preferably 1 to 18 carbon atoms. The alkyl moiety in the aforementioned substituted alkyl group is the same as the above mentioned alkyl group. The aforementioned alkenyl group may have a branch or may form a ring (i.e. a cycloalkenyl group). The alkenyl group has preferably 2 to 20 carbon atoms, and more preferably 2 to 18 carbon atoms. The alkenyl moiety in the aforementioned substituted alkenyl group is the same as the above mentioned alkenyl group. The aforementioned alkynyl group may have a branch or may form a ring (i.e. a cycloalkynyl group). The alkynyl group has preferably 2 to 20 carbon atoms, and more preferably 2 to 18 carbon atoms. The alkynyl moiety in the aforementioned substituted alkynyl group is the same as the above mentioned alkynyl group. The alkyl moiety in the aforementioned aralkyl group and substituted aralkyl group is the same as the above mentioned alkyl group. The aryl moiety in the aforementioned aralkyl group and substituted aralkyl group is the same as the aryl group mentioned below.

Specific examples of the substituent in the substituted alkyl group, the substituted alkenyl group, the substituted alkynyl group, and the alkyl moiety in the substituted aralkyl group include: a halogen atom (e.g. a chlorine atom, a bromine atom, or an iodine atom); an alkyl group which represents a substituted or unsubstituted linear, branched, or cyclic alkyl group, and which includes an alkyl group (preferably an alkyl group having 1 to 30 carbon atoms, e.g. a methyl group, an ethyl group, an n-propyl group, an isopropyl group, a t-butyl group, an n-octyl group, an eicosyl group, a 2-chloroethyl group, a 2-cyanoethyl group, or a 2-ethylhexyl group), a cycloalkyl group (preferably a substituted or unsubstituted cycloalkyl group having 3 to 30 carbon atoms, e.g. a cyclohexyl group, a cyclopentyl group, or a 4-n-dodecylcyclohexyl group), a bicycloalkyl group (preferably a substituted or unsubstituted bicycloalkyl group having 5 to 30 carbon atoms, i.e. a monovalent group obtained by removing one hydrogen atom from a bicycloalkane having 5 to 30 carbon atoms, e.g. a bicyclo[1,2,2]heptan-2-yl group or a bicyclo[2,2,2]octan-3-yl group), and a tricyclo or higher structure having three or more ring structures; and an alkyl group in a substituent explained below (e.g. an alkyl group in an alkylthio group) represents such an alkyl group of the above concept]; an alkenyl group which represents a substituted or unsubstituted linear, branched, or cyclic alkenyl group, and which includes an alkenyl group (preferably a substituted or unsubstituted alkenyl group having 2 to 30 carbon atoms, e.g. a vinyl group, an allyl group, a prenyl group, a geranyl group, or an oleyl group), a cycloalkenyl group (preferably a substituted or unsubstituted cycloalkenyl group having 3 to 30 carbon atoms, i.e. a monovalent group obtained by removing one hydrogen atom from a cycloalkene having 3 to 30 carbon atoms, e.g. a 2-cyclopenten-1-yl group or a 2-cyclohexen-1-yl group), and a bicycloalkenyl group (which represents a substituted or unsubstituted bicycloalkenyl group, preferably a substituted or unsubstituted bicycloalkenyl group having 5 to 30 carbon atoms, i.e. a monovalent group obtained by removing one hydrogen atom from a bicycloalkene having one double bond, e.g. a bicyclo[2,2,1]hept-2-en-1-yl group or a bicyclo[2,2,2]oct-2-en-4-yl group)]; an alkynyl group (preferably a substituted or unsubstituted alkynyl group having 2 to 30 carbon atoms, e.g. an ethynyl group, a propargyl group, or a trimethylsilylethynyl group); an aryl group (preferably a substituted or unsubstituted aryl group having 6 to 30 carbon atoms, e.g. a phenyl group, a p-tolyl group, a naphthyl group, an m-chlorophenyl group, or an o-hexadecanoylaminophenyl group); a heterocyclic group (preferably a monovalent group obtained by removing one hydrogen atom from a substituted or unsubstituted 5- or 6-membered aromatic or nonaromatic heterocyclic compound; more preferably a 5- or 6-membered aromatic heterocyclic group having 3 to 30 carbon atoms, e.g. a 2-furyl group, a 2-thienyl group, a 2-pyrimidinyl group, a 2-benzothiazolyl group); a cyano group; a hydroxy group; a nitro group; a carboxyl group; an alkoxy group (preferably a substituted or unsubstituted alkoxy group having 1 to 30 carbon atoms, e.g. a methoxy group, an ethoxy group, an isopropoxy group, a t-butoxy group, an n-octyloxy group, or a 2-methoxyethoxy group); an aryloxy group (preferably a substituted or unsubstituted aryloxy group having 6 to 30 carbon atoms, e.g. a phenoxy group, a 2-methylphenoxy group, a 4-t-butylphenoxy group, a 3-nitrophenoxy group, or a 2-tetradecanoylaminophenoxy group); a silyloxy group (preferably a silyloxy group having 3 to 20 carbon atoms, e.g. a trimethylsilyloxy group or a t-butyldimethylsilyloxy group); a heterocyclic oxy group (preferably a substituted or unsubstituted heterocyclic oxy group having 2 to 30 carbon atoms, e.g. a 1-phenyltetrazol-5-oxy group or a 2-tetrahydropyranyloxy group); an acyloxy group (preferably a formyloxy group, a substituted or unsubstituted alkylcarbonyloxy group having 2 to 30 carbon atoms, or a substituted or unsubstituted arylcarbonyloxy group having 7 to 30 carbon atoms, e.g. a formyloxy group, an acetyloxy group, a pivaloyloxy group, a stearoyloxy group, a benzoyloxy group, or a p-methoxyphenylcarbonyloxy group); a carbamoyloxy group (preferably a substituted or unsubstituted carbamoyloxy group having 1 to 30 carbon atoms, e.g. an N,N-dimethylcarbamoyloxy group, an N,N-diethylcarbamoyloxy group, a morpholinocarbonyloxy group, an N,N-di-n-octylaminocarbo-
nyloxy group, or an N-n-octylcarbamoyloxy group); an alkoxycarbonyloxy group (preferably a substituted or unsubstituted alkoxycarbonyloxy group having 2 to 30 carbon atoms, e.g. a methoxycarbonyloxy group, an ethoxycarbonyloxy group, a t-butoxycarbonyloxy group, or an n-octylcarbonyloxy group); an aryloxycarbonyloxy group (preferably a substituted or unsubstituted aryloxycarbonyloxy group having 7 to 30 carbon atoms, e.g. a phenoxycarbonyloxy group, a p-methoxyphenoxycarbonyloxy group, or a p-n-hexadecyloxyphenoxycarbonyloxy group); an amino group (preferably an amino group, a substituted or unsubstituted alkylamino group having 1 to 30 carbon atoms, or a substituted or unsubstituted anilino group having 6 to 30 carbon atoms, e.g. an amino group, a methylamino group, a dimethylamino group, an anilino group, an N-methyl-anilino group, or a diphenylamino group); an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, e.g. a formylamino group, an acetylamino group, a pivaloylamino group, a lauroylamino group, a benzoylamino group, or a 3,4,5-tri-n-octyloxyphenylcarbonylamino group); an aminocarbonylamino group (preferably a substituted or unsubstituted aminocarbonylamino group having 1 to 30 carbon atoms, e.g. a carbamoylamino group, an N,N-dimethylaminocarbonylamino group, an N,N-diethylaminocarbonylamino group, or a morpholinocarbonylamino group); an alkoxycarbonylamino group (preferably a substituted or unsubstituted alkoxycarbonylamino group having 2 to 30 carbon atoms, e.g. a methoxycarbonylamino group, an ethoxycarbonylamino group, a t-butoxycarbonylamino group, an n-octadecyloxycarbonylamino group, or an N-methyl-methoxycarbonylamino group); an aryloxycarbonylamino group (preferably a substituted or unsubstituted aryloxycarbonylamino group having 7 to 30 carbon atoms, e.g. a phenoxycarbonylamino group, a p-chlorophenoxycarbonylamino group, or an m-n-octyloxyphenoxycarbonylamino group); a sulfamoylamino group (preferably a substituted or unsubstituted sulfamoylamino group having 0 to 30 carbon atoms, e.g. a sulfamoylamino group, an N,N-dimethylaminosulfonylamino group, or an N-n-octylaminosulfonylamino group); an alkyl- or aryl-sulfonylamino group (preferably a substituted or unsubstituted alkylsulfonylamino group having 1 to 30 carbon atoms, or a substituted or unsubstituted arylsulfonylamino group having 6 to 30 carbon atoms, e.g. a methylsulfonylamino group, a butylsulfonylamino group, a phenylsulfonylamino group, a 2,3,5-trichlorophenylsulfonylamino group, or a p-methylphenylsulfonylamino group); a mercapto group; an alkylthio group (preferably a substituted or unsubstituted alkylthio group having 1 to 30 carbon atoms, e.g. a methylthio group, an ethylthio group, or an n-hexadecylthio group); an arylthio group (preferably a substituted or unsubstituted arylthio group having 6 to 30 carbon atoms, e.g. a phenylthio group, a p-chlorophenylthio group, or an m-methoxyphenylthio group); a heterocyclic thio group (preferably a substituted or unsubstituted heterocyclic thio group having 2 to 30 carbon atoms, e.g. a 2-benzothiazolylthio group or a 1-phenyltetrazol-5-ylthio group); a sulfamoyl group (preferably a substituted or unsubstituted sulfamoyl group having 0 to 30 carbon atoms, e.g. an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, or an N—(N'-phenylcarbamoyl)sulfamoyl group); a sulfo group; an alkyl- or aryl-sulfonyl group (preferably a substituted or unsubstituted alkylsulfonyl group having 1 to 30 carbon atoms, or a substituted or unsubstituted arylsulfinyl group having 6 to 30 carbon atoms, e.g. a methylsulfonyl group, an ethylsulfinyl group, a phenylsulfinyl group, or a p-methylphenylsulfinyl group); an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g. a methylsulfonyl group, an ethylsulfonyl group, a phenylsulfonyl group, or a p-methylphenylsulfonyl group); an acyl group (preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms and being bonded to said carbonyl group through a carbon atom, e.g. an acetyl group, a pivaloyl group, a 2-chloroacetyl group, a stearoyl group, a benzoyl group, a p-n-octyloxyphenylcarbonyl group, a 2-pyridylcarbonyl group, or a 2-furylcarbonyl group); an aryloxycarbonyl group (preferably a substituted or unsubstituted aryloxycarbonyl group having 7 to 30 carbon atoms, e.g. a phenoxycarbonyl group, an o-chlorophenoxycarbonyl group, an m-nitrophenoxycarbonyl group, or a p-t-butylphenoxycarbonyl group); an alkoxycarbonyl group (preferably a substituted or unsubstituted alkoxycarbonyl group having 2 to 30 carbon atoms, e.g. a methoxycarbonyl group, an ethoxycarbonyl group, a t-butoxycarbonyl group, or an n-octadecyloxycarbonyl group); a carbamoyl group (preferably a substituted or unsubstituted carbamoyl group having 1 to 30 carbon atoms, e.g. a carbamoyl group, an N-methylcarbamoyl group, an N,N-dimethylcarbamoyl group, an N,N-di-n-octylcarbamoyl group, or an N-(methylsulfonyl)carbamoyl group); an aryl- or heterocyclic-azo group (preferably a substituted or unsubstituted aryl azo group having 6 to 30 carbon atoms, or a substituted or unsubstituted heterocyclic azo group having 3 to 30 carbon atoms, e.g. a phenylazo group, a p-chlorophenylazo group, or a 5-ethylthio-1,3,4-thiadiazol-2-ylazo group); an imido group (preferably an N-succinimido group or an N-phthalimido group); a phosphino group (preferably a substituted or unsubstituted phosphino group having 2 to 30 carbon atoms, e.g. a dimethylphosphino group, a diphenylphosphino group, or a methylphenoxyphosphino group); a phosphinyl group (preferably a substituted or unsubstituted phosphinyl group having 2 to 30 carbon atoms, e.g. a phosphinyl group, a dioctyloxyphosphinyl group, or a diethoxyphosphinyl group); a phosphinyloxy group (preferably a substituted or unsubstituted phosphinyloxy group having 2 to 30 carbon atoms, e.g. a diphenoxyphosphinyloxy group or a dioctyloxyphosphinyloxy group); a phosphinylamino group (preferably a substituted or unsubstituted phosphinylamino group having 2 to 30 carbon atoms, e.g. a dimethoxyphosphinylamino group or a dimethylaminophosphinylamino group); and a silyl group (preferably a substituted or unsubstituted silyl group having 3 to 30 carbon atoms, e.g. a trimethylsilyl group, a t-butyldimethylsilyl group, or a phenyldimethylsilyl group).

Among the above functional groups, those having a hydrogen atom may further be substituted with any of the above groups at the position from which the hydrogen atom is removed. Examples of such a functional group include an alkylcarbonylaminosulfonyl group, an arylcarbonylaminosulfonyl group, an alkylsulfonylaminocarbonyl group, and an arylsulfonylaminocarbonyl group. Specific examples of these groups include a methylsulfonylaminocarbonyl, a p-methylphenylsulfonylaminocarbonyl, an acetylaminosulfonyl, and a benzoylaminosulfonyl group.

Examples of the substituent on the aryl moiety of the substituted aralkyl group include substituents of the following substituted aryl groups.

The aromatic group in this specification means an aryl group or a substituted aryl group. Further, these aromatic groups may be condensed with aliphatic rings, other aromatic rings or hetero rings. The number of carbon atoms of the aromatic group is preferably 6 to 40, more preferably 6 to 30, and still more preferably 6 to 20. Among these groups, the aryl group is preferably phenyl or naphthyl, and particularly preferably phenyl.

The aryl moiety of the substituted aryl group is the same as the above aryl group. Examples of the substituent of the substituted aryl group include those given above as the substituents of the substituted alkyl group, the substituted alkenyl group, the substituted alkynyl group, and the alkyl moiety of the substituted aralkyl group.

In the present specification, a heterocyclic group preferably contains a 5- or 6-membered saturated or unsaturated heterocycle. Such a heterocycle may be condensed with an aliphatic ring, an aromatic ring, or another heterocycle. Examples of the heteroatom in the heterocycle include boron (B), nitrogen (N), oxygen (O), sulfur (S), selenium (Se) and Tellurium (Te). As a heteroatom, nitrogen (N), oxygen (O) or sulfur (S) are preferable. The heterocycle preferably has a free monovalent carbon atom (the heterocyclic group binds at the carbon atom). The heterocyclic group has preferably 1 to 40 carbon atoms, more preferably 1 to 30 carbon atoms, and further more preferably 1 to 20 carbon atoms. Examples of the saturated heterocycle include a pyrrolidine ring, a morpholine ring, 2-bora-1,3-dioxolan ring, and 1,3-thiazolidine ring. Examples of the unsaturated heterocycle include an imidazole ring, a thiazole ring, a benzothiazole ring, a benzoxazole ring, a benzotriazole ring, a benzoselenazole ring, a pyridine ring, a pyrimidine ring, and a quinoline ring. The heterocyclic group may have a substituent or substituents. Examples of the substituent include the substituents listed above as the substituents for the substituted alkyl group, the substituted alkenyl group, the substituted alkynyl group, and the alkyl moiety of the substituted aralkyl group.

Next, the compounds represented by formulae (I) to (II) are explained below. In formulae (I) to (II), $R_1$ represents a substituent. Examples of the substituent on $R_1$ include the substituents listed above for the substituted alkyl group, the substituted alkenyl group, the substituted alkynyl group, and the alkyl moiety of the substituted aralkyl group.

Preferred examples of $R_1$ include a halogen atom, an alkyl group, an alkenyl group, an alkynyl group, an aryl group, a cyano group, a hydroxy group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkyl thio group, an aryl thio group, a heterocyclic thio group, a sulfamoyl group, a sulfo group, an alkyl sulfinyl group, an aryl sulfinyl group, an alkyl sulfonyl group, an aryl sulfonyl group, an acyl group, an aryloxycarbonyl group, an alkoxycarbonyl group, a carbamoyl group, an imido group, a phosphino group, a phosphinyl group, a phosphinyloxy group, a phosphinylamino group, and a silyl group. More preferred examples of $R_1$ include a halogen atom, an alkyl group, an aryl group, a cyano group, a hydroxy group, a nitro group, a carboxyl group, an alkoxy group, an aryloxy group, a silyloxy group, a heterocyclic oxy group, an acyloxy group, a carbamoyloxy group, an amino group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkyl thio group, an aryl thio group, a heterocyclic thio group, a sulfamoyl group, a sulfo group, an alkyl sulfinyl group, an aryl sulfinyl group, an alkyl sulfonyl group, an aryl sulfonyl group, a carbamoyl group, an imido group, a phosphino group, a phosphinyl group, a phosphinyloxy group, a phosphinylamino group and a silyl group. Furthermore preferred examples of $R_1$ include a halogen atom, an alkyl group, an aryl group, a hydroxy group, an alkoxy group, an aryloxy group, an amino group, a mercapto group, an alkyl thio group, an aryl thio group, a sulfamoyl group, a sulfo group, an alkyl sulfinyl group, an aryl sulfinyl group, an alkyl sulfonyl group and an aryl sulfonyl group. Furthermore preferred examples of $R_1$ include a halogen atom, an alkyl group, an aryl group, an alkoxy group, an aryloxy group, an alkyl thio group and an aryl thio group. Furthermore preferred examples of $R_1$ include a halogen atom, an alkyl group having 1 to 20 carbon atoms, an aryl group having 6 to 20 carbon atoms, an alkoxy group having 1 to 20 carbon atoms, an aryloxy group having 6 to 20 carbon atoms, an alkyl thio group having 1 to 20 carbon atoms and an aryl thio group having 6 to 20 carbon atoms. Furthermore preferred examples of $R_1$ include a chlorine atom, a fluorine atom, a bromine atom, an alkyl group having 1 to 8 carbon atoms, an aryl group having 6 to 10 carbon atoms, an alkoxy group having 1 to 8 carbon atoms, an aryloxy group having 6 to 10 carbon atoms, an alkyl thio group having 1 to 8 carbon atoms and an aryl thio group having 6 to 10 carbon atoms. Furthermore preferred examples of $R_1$ include a chlorine atom, a fluorine atom, an alkyl group having 1 to 4 carbon atoms and an alkoxy group having 1 to 4 carbon atoms.

$n_1$ is preferably 0 to 3, more preferably 0 to 2, still more preferably 0 or 1, and most preferably 0, i.e., the benzene ring has no substituent.

$R_2$ represents an $n_2$-valent substituent or a linking group, and examples of the substituent include substituents similar to those on the alkyl units in the substituted alkyl groups, substituted alkenyl groups, substituted alkynyl groups and substituted aralkyl groups described above. The linking group is a substituent having one or more additional binding sites.

$R_2$ preferably represents an aliphatic group, an aromatic group, a heterocyclic group, or a linking group thereof having another binding site; more preferably an alkyl group, an alkenyl group, an alkynyl group, an aryl group, a heterocyclic group of N, O, or S and carbon atoms, or a bivalent to tetravalent linking group thereof; still more preferably, an alkyl group, an alkenyl group, an aryl group, a heterocyclic group of N, O, or S and carbon atoms, or a bivalent to trivalent linking group thereof; still more preferably an alkyl group having 1 to 20 carbon atoms, an alkenyl group having 2 to 20 carbon atoms, an aryl group having 6 to 20 carbon atoms, a five- or six-membered heterocyclic group of N, O, or S and carbon atoms, or a bivalent or trivalent linking group thereof; still more preferably an alkyl group having 1 to 8 carbon atoms, an alkenyl group having 2 to 8 carbon atoms, an aryl group having 6 to 12 carbon atoms, a five- or six-membered heterocyclic group of N, O, or S and carbon atoms, or a bivalent to trivalent linking group thereof; still more preferably, an alkyl group having 1 to 8 carbon atoms, an aryl group having 6 to 12 carbon atoms, a five- or six-membered heterocyclic group of N, O, or S and carbon atoms, or a bivalent to trivalent linking group thereof; still more preferably, methyl, ethyl, propyl, butyl, isopropyl, 2-butyl, benzyl, phenyl, 2-naphthyl, pyrrol-2-yl, thiophen-2-yl, indol-1-yl, indol-2-yl, benzofuran-2-yl, benzothiophen-2-yl, ethylene, trimethylene, 1,2-propylene, tetramethylene, 1,2-phenylene, 1,3-phenylene, 1,4-phenylene, 2,6-naphthylene, furan-2,5-yl, thiophene-2,5-yl, or benzene-1,3,5-yl; still more preferably, methyl, ethyl, benzyl, phenyl, pyrrol-2-yl, thiophen-2-yl, indol-1-yl, indol-2-yl, benzothiophen-2-yl, ethylene, trimethylene, 1,3-phenylene, 1,4-phenylene, pyrrole-2,5-yl, thiophene-2,5-yl, or benzene-1,3,5-yl; still more preferably ethylene, trimethylene, 1,3-phenylene, 1,4-phenylene, pyrrole-2,5-yl, thiophene-2,5-yl, or benzene-1,3,5-yl; and most preferably, 1,4-phenylene.

$n_2$ is preferably 1 to 3, more preferably 2 to 3, and most preferably 2.

Next, specific examples of the compounds represented by formula (I) are shown below. However, the present invention should not be construed as being limited to these compounds.

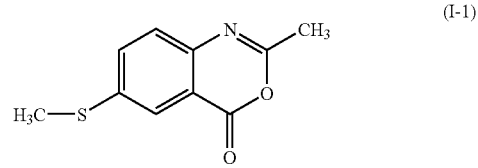

(I-1)

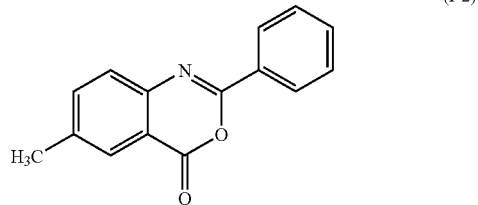

(I-2)

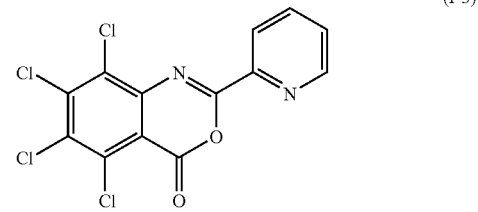

(I-3)

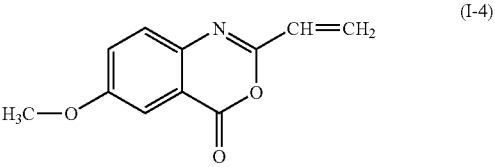

(I-4)

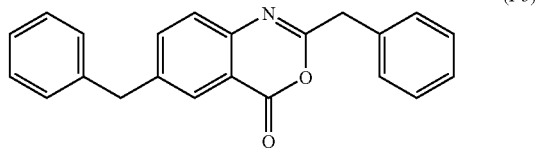

(I-5)

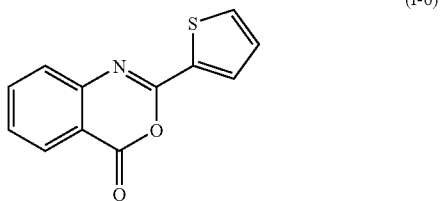

(I-6)

(I-7)
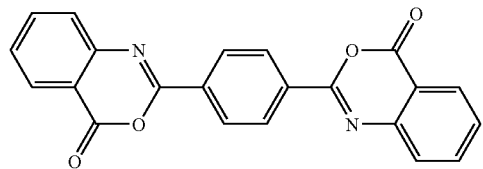
(I-8)
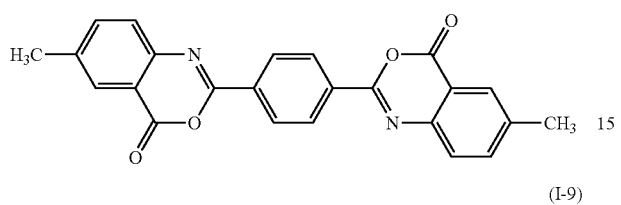
(I-9)
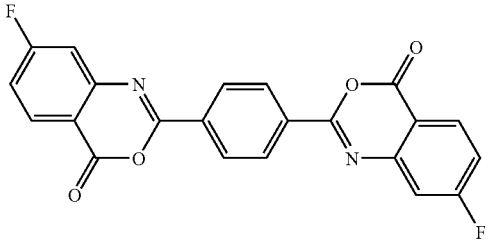
(I-10)
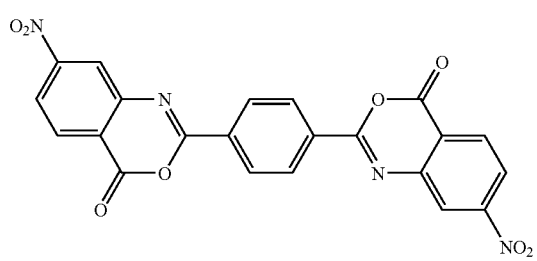
(I-11)
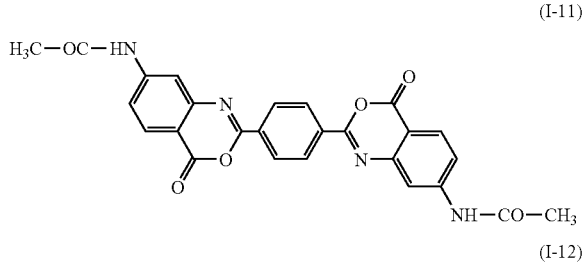
(I-12)
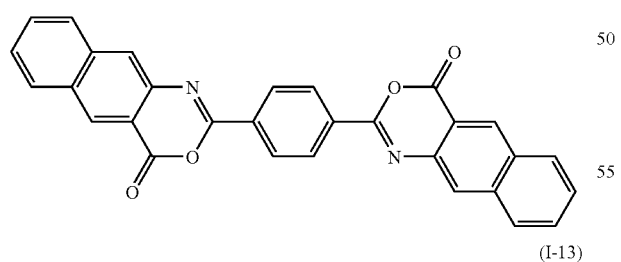
(I-13)
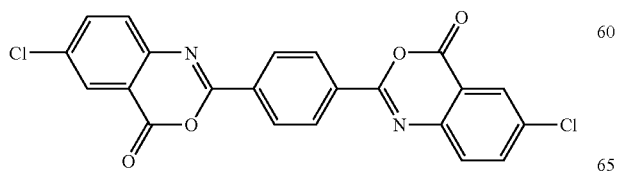
(I-14)
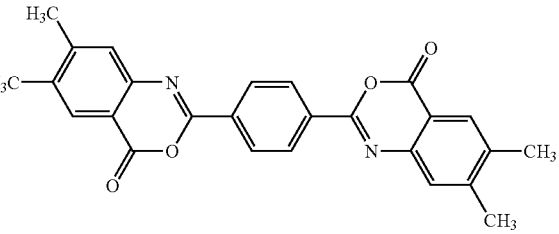
(I-15)
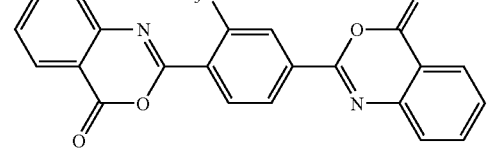
(I-16)
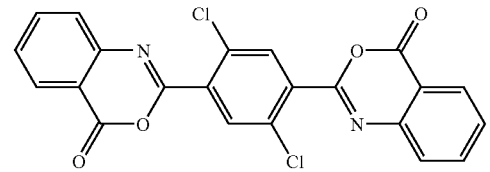
(I-17)
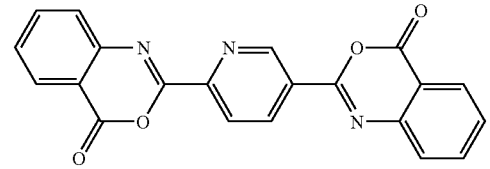
(I-18)
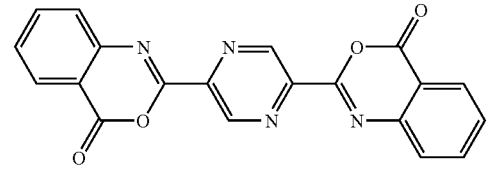
(I-19)
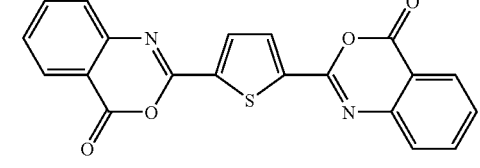
(I-20)
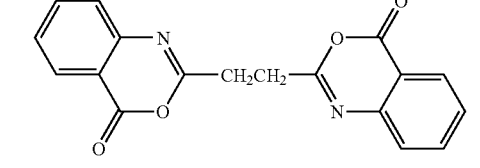
(I-21)
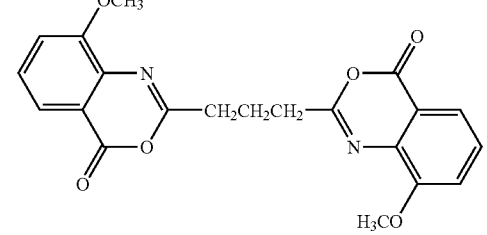

-continued

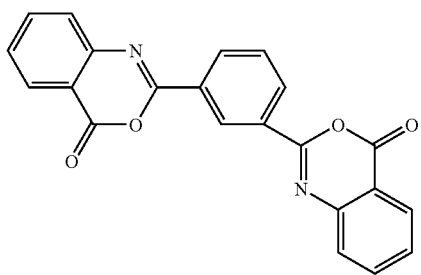
(I-22)

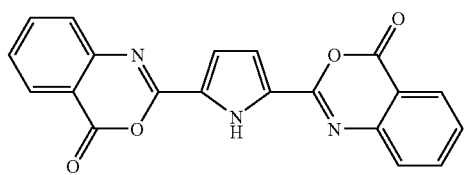
(I-23)

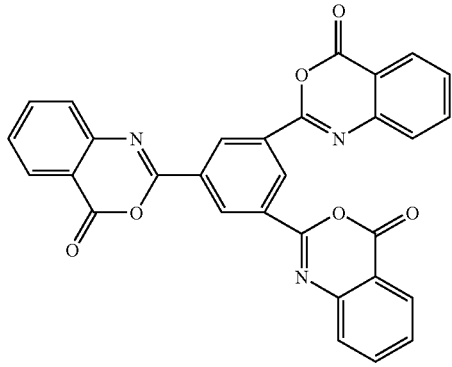
(I-24)

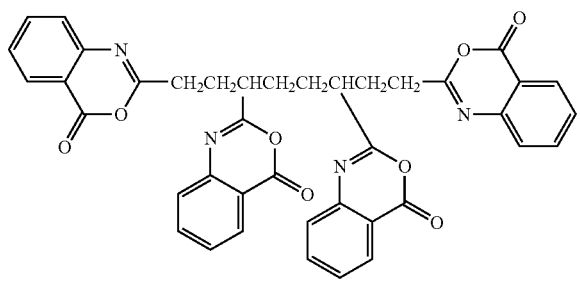
(I-25)

Hereinafter, the method of producing the compound represented by Formula (I) according to the present invention will be described. The method of producing the compound represented by Formula (I) according to the present invention includes a step A of reacting an anthranilic acid compound with a carboxylic halide in the absence of base. The amide intermediate is formed in the step A. Also in the present invention, the amide intermediate prepared in the step A is converted into a benzoxazinone skeleton-containing compound by dehydration condensation in step B, to give the compound represented by Formula (I). In this case, the reaction mixture including the amide intermediate prepared in Step A is preferably subjected to Step B as it is.

The raw material anthranilic acid compound for use may be a substituted or unsubstituted anthranilic acid. The substituted anthranilic acid is, for example, a compound of which hydrogen atoms on the anthranilic acid benzene ring are replaced with $n_1$ pieces of substituents $R_1$, wherein, $R_1$ represents a substituent and $n_1$ is an integer of 0 to 4. $R_1$ and $n_1$ are respectively the same as those in Formula (I) above, and the favorable ranges are also the same.

The raw material carboxylic halide is represented by $R_2(-COX)_{n_2}$. In the formula, $R_2$ represents an $n_2$-valent substituent or a linking group, and $n_2$ is an integer of 1 to 4. X represents a halogen atom. $R_2$ and $n_2$ are respectively the same as those shown in Formula (I), and the preferable ranges are also the same.

The raw material carboxylic halide for use is prepared by acid halogenation of the carboxylic acid compound.

Examples of the acid halogenating agents for use in preparation of the carboxylic halide include thionyl chloride, oxalyl chloride, phosphorus oxychloride, phosphorus trichloride, phosphorus pentachloride, and the like; favorable examples thereof include thionyl chloride, oxalyl chloride, and phosphorus oxychloride; still more preferable are thionyl chloride and oxalyl chloride; and most preferable is thionyl chloride.

The solvent for use in preparation of the carboxylic halide is preferably the solvent used in steps A and B. Particularly preferable is a non-polar solvent.

The reaction temperature in preparation of the carboxylic halide is normally −20 to 100° C., preferably 20 to 90° C., still more preferably 40 to 80° C., still more preferably 60 to 75° C., and particularly preferably 70 to 73° C.

As for the ratio of the raw materials in preparation of the carboxylic halide, the acid halogenating agent is used preferably in an amount of 0.8 to 5.0 moles, more preferably 1.0 to 3.0 moles, still more preferably 1.0 to 2.0 moles, still more preferably 1.0 to 1.5 moles, still more preferably 1.0 to 1.3 moles, and most preferably 1.0 to 1.1 moles, with respect to one carboxyl group of the carboxylic acid compound.

The carboxylic halide prepared is preferably supplied as it is without isolation to the step A. In other words, the reaction mixture including the carboxylic halide thus prepared is preferably used in Step A as it is.

Hereinafter, the step A and the subsequent step will be described.

As for the ratio of the raw materials for use in the present reaction, the $n_2$-valent carboxylic halide is used preferably in an amount of $0.3/n_2$ to $2.0/n_2$ moles, more preferably $0.6/n_2$ to $1.5/n_2$ moles, and still more preferably $0.8/n_2$ to $1.2/n_2$ moles, with respect to 1 mole of the anthranilic acid compound.

The reaction may be carried out in the presence or absence of a solvent, preferably in the presence of a solvent. Examples of the solvents, if used, amide solvents (e.g., N,N-dimethylformamide, N,N-dimethylacetamide and N-methylpyrrolidinone), sulfone solvent (e.g., sulfolane), ureide solvents (e.g., 1-methyl-2-imidazolidinone), urea solvents (e.g., tetramethylurea), ether solvents (e.g., dioxane and cyclopentylmethylether), ketone solvents (e.g., acetone, methylethylketone and cyclohexanone), hydrocarbon solvents (e.g., toluene, xylene and n-decane), halogenated solvents (e.g., tetrachloroethane and chlorobenzene), alcohol solvents (e.g., methanol, ethanol, isopropyl alcohol, ethylene glycol, cyclohexanol and phenol), ester solvents (e.g., ethyl acetate and butyl acetate), nitrile solvents (e.g., acetonitrile), water, and the like, and these solvents may be used alone or as a mixture. It is also favorable to add the same or another solvent in step B after completion of the step A.

In step A, it is preferred that no protic solvent is used. Examples of the protic solvent include carboxylic acid series solvents such as acetic acid, alcoholic solvents such as methanol and isopropanol, and water. On the contrary, it is preferred that an aprotic solvent is used in step A. The carboxylic halide used as the raw material in step A is known to decompose gradually with protic solvents such as alcohols, and thus, use of a protic solvent leads to decrease in yield.

In addition, a solvent having a donor number of 10 or more is used favorably as the solvent both in steps A and B. The donor number of solvent is described in detail, for example, in V. Gutmann, translated by Hitoshi Otaki and Isato Okada, "Donor to Acceptor: Yoeki•Hanno no Bunshikan-sogo-sayo (Intermolecular interaction in solution reaction between donor and acceptor)" 1983, (Japan Scientific Societies Press) p. 21 to 29. The solvents for use in the present invention are not limited to those having an known donor number, as described in these literatures, and thus, solvents having no known value but seemingly having a value in the favorable range if determined according to the method described in literature are also included.

The donor number of solvent is more preferably 15 or more, still more preferably 20 or more, and still more preferably 25 or more. The upper limit of the donor number is not particularly limited, but it is generally 50, and preferably 40. Examples of the solvents having a donor number of 15 or more favorably used in the present invention include ethylene carbonate (DN:16.4, hereinafter "DN" represents donor number), acetone (DN:17.0), ethyl acetate (DN:17.1), tetrahydrofuran (DN:20.0), N,N-dimethylformamide (DN:26.6), N,N-dimethylacetamide (DN:27.8), N-methylpyrrolidinone (DN: 27.3), hexamethylphosphoric triamide (DN:38.8), and the like, and more preferable are N,N-dimethylformamide, N,N-dimethylacetamide, and N-methylpyrrolidinone.

The reaction temperature of step A is normally −50 to 100° C., preferably −40 to 70° C., more preferably −30 to 50° C., still more preferably −20 to 30° C., still more preferably −15 to 20° C., still more preferably −10 to 10° C., and particularly preferably 0 to 10° C.

Alternatively, the reaction temperature of step B is normally 0 to 200° C., preferably 30 to 180° C., still more preferably 50 to 150° C., and particularly preferably 80 to 130° C.

In step B, copresence of at least one dehydrating condensing agent is preferable. Examples of favorable dehydrating condensing agents include inorganic dehydrating condensing agents (e.g., acid anhydrides such as sulfuric anhydride and diphosphoric pentoxide and acid chlorides such as thionyl chloride and phosphorus oxychloride), organic dehydrating condensing agents (e.g., acid anhydrides such as acetic anhydride and propionic anhydride, acid halides such as acetyl chloride, N,N-dicyclohexyl carbodiimide, etc.), adsorbents such as molecular sieves, and inorganic compounds incorporating water as crystal solvent such as anhydrous sodium sulfate. Particularly preferable among them are inorganic and organic dehydrating condensing agents; still more preferable are inorganic or organic acid anhydrides; still more preferable are organic acid anhydrides; and most preferable is acetic anhydride.

In the method according to the present invention, a benzoxazinone-based compound useful as the ultraviolet absorbent for thermoplastic polymers can be produced inexpensively and effectively at high purity. Conventional methods, such as the method described in JP-A-2000-264879, use an alkali and thus had high possibility of the alkali being contaminated in the final product, because the intermediate was not isolated. The contamination of the alkali in the final product is undesirable from the point of storage life. In contrast, the method according to the present invention, wherein no alkali is used, does not cause such a problem.

The method according to the present invention provides a benzoxazinone-based compound useful as an ultraviolet absorbent for thermoplastic polymers inexpensively and effectively at high purity.

The present invention will be described in more detail based on the following examples, but the present invention is not limited thereto.

EXAMPLES

Example 1

Preparation of Exemplified Compound (I-7)

120.7 g of anthranilic acid and 1000 ml of N-methylpyrrolidinone were placed in a three-necked flask, and the mixture was dissolved while agitated. 89.3 g of terephthaloyl chloride (terephthalic dichloride) was added to the solution while agitated on ice, and the mixture was agitated additionally for 2 hours. The internal temperature was 3 to 8° C. at the time. Then, 225 g of acetic anhydride and 500 ml of N-methylpyrrolidinone were added thereto, the mixture was heated while stirred at an internal temperature of 108 to 116° C. for 2 hours and then cooled to 30° C. or lower; and the crystal obtained was filtered and dried, to give 155.6 g of a target exemplified compound (I-7) (yield: 96%). The content of sodium and potassium in the exemplified compound obtained (I-7) was 1 ppm or less. The lower detection limits for sodium and potassium are 1 ppm respectively, which is applicable to Examples 2 to 8.

Melting point: 317.3° C.

Maximum absorption wavelength ($\lambda$ max) in solution: 349.5 nm (toluene solution)

Example 2

Preparation of Exemplified Compound (I-7)

120.7 g of anthranilic acid and 1000 ml of N,N-dimethylacetamide were placed in a three-necked flask, and the mixture was dissolved while agitated. 89.3 g of terephthaloyl chloride was added to the mixture while the mixture was stirred continuously; the resulting solution was cooled in an ice-methanol bath; and the mixture was agitated additionally for 1 hour. The internal temperature was 0 to 5° C. at the time. Then, 225 g of acetic anhydride and 500 ml of toluene were added thereto; the mixture was heated and agitated under solvent reflux for 1.5 hours and then cooled to 30° C. or lower; and the crystal obtained was filtered and dried, to give 160.5 g of a target exemplified compound (I-7) (yield: 99%). The content of sodium and potassium in the exemplified compound obtained (I-7) was 1 ppm or less.

Melting point: 316.3° C.

Maximum absorption wavelength ($\lambda$ max) in solution: 349.5 nm (toluene solution)

Example 3

Preparation of Exemplified Compound (I-7)

120.7 g of anthranilic acid and 1000 ml of sulfolane were placed in a three-necked flask, and the mixture was dissolved while agitated. 89.3 g of terephthaloyl chloride was added to the solution while agitated on ice, and the mixture was agitated additionally for 2 hours. The internal temperature was 6 to 8° C. then. 225 g of acetic anhydride and 500 ml of dioxane were added thereto, the mixture was heated while agitated under reflux for 2 hours and then cooled to 30° C. or lower; and the crystal obtained was filtered and dried, to give 155.6 g of a target exemplified compound (I-7) (yield: 96%). The content of sodium and potassium in the exemplified compound obtained (I-7) was 1 ppm or less.

Melting point: 316.5° C.

Maximum absorption wavelength (λ max) in solution: 349.5 nm (toluene solution)

Example 4

Preparation of Exemplified Compound (I-8)

151.1 g of 2-amino-5-methybenzoic acid and 1200 ml of N,N-dimethylacetamide were placed in a three-necked flask, and the mixture was dissolved while agitated. 101.5 g of terephthaloyl chloride was added to the mixture while the mixture was stirred continuously; the resulting solution was cooled in an ice-methanol bath; and the mixture was agitated additionally for 2 hours. The internal temperature was −3 to 4° C. at the time. Then, 254 g of acetic anhydride and 600 ml of toluene were added thereto; the mixture was heated and agitated under solvent reflux for 1.5 hours and then cooled to 30° C. or lower; and the crystal obtained was filtered and dried, to give 194.2 g of a target exemplified compound (I-8) (yield: 98%). The content of sodium and potassium in the exemplified compound obtained (I-8) was 1 ppm or less.

Example 5

Preparation of Exemplified Compound (I-13)

171.6 g of 2-amino-5-chlorobenzoic acid and 1400 ml of N,N-dimethylacetamide were placed in a three-necked flask, and the mixture was dissolved while agitated. 101.5 g of terephthaloyl chloride was added to the solution while agitated on ice, and the mixture was agitated additionally for 4 hours. The internal temperature was 4 to 11° C. then. 254 g of acetic anhydride and 600 ml of N-dimethylacetamide were then added thereto; the mixture was heated while stirred at an internal temperature of 105 to 126° C. for 2 hours, and then, cooled to 30° C. or lower; and the crystal obtained was filtered and dried, to give 212.1 g of a target exemplified compound (I-13) (yield: 97%). The content of sodium and potassium in the exemplified compound (I-13) obtained was 1 ppm or less.

Example 6

Preparation of Exemplified Compound (I-6)

13.7 g of anthranilic acid and 100 ml of N,N-dimethylacetamide were placed in a three-necked flask, and the mixture was dissolved while agitated. 14.7 g of 2-thiophene carbonyl chloride was added to the solution while agitated on ice, and the mixture was agitated additionally for 4 hours. The internal temperature was 7 to 13° C. then. 25 g of acetic anhydride and 50 ml of N,N-dimethylacetamide were then added thereto; the mixture was heated while stirred at an internal temperature of 98 to 118° C. for 2 hours, and then, cooled to 30° C. or lower; and the crystal obtained was filtered and dried, to give 21.8 g of a target exemplified compound (I-6) (yield: 95%). The content of sodium and potassium in the exemplified compound (I-6) obtained was 1 ppm or less.

Example 7

Preparation of Exemplified Compound (I-7)

73.1 g of terephthalic acid and 280 ml of toluene were placed in a three-necked flask, and the mixture was agitated while cooled on ice. 157.1 g of thionyl chloride was added dropwise thereto; the mixture was heated while agitated at an internal temperature of 50 to 75° C. for 7 hours, and then cooled to 30° C. or lower. 280 ml of water was added thereto; the mixture was agitated for 5 minutes; and then the aqueous phase was removed. It was added to a mixture of 120.7 g of anthranilic acid and 1000 ml of N,N-dimethylacetamide placed in a three-necked flask that was previously dissolved by agitation and agitated continuously as cooled in an ice-methanol bath, and the resulting mixture was stirred additionally for 1 hour. The internal temperature was 0 to 5° C. at the time. Then, 225 g of acetic anhydride and 220 ml of toluene were added thereto; the mixture was agitated and heated under solvent reflux for 1.5 hours and then cooled to 30° C. or lower; and the resulting crystal was filtered and dried, to give 160.5 g of a target exemplified compound (I-7) (yield: 96%). The content of sodium and potassium in the exemplified compound (I-7) obtained was 1 ppm or less.

Example 8

Preparation of Exemplified Compound (I-8)

83.1 g of terephthalic acid and 300 ml of toluene were placed in a three-necked flask, and the mixture was agitated while cooled on ice. 178.5 g of thionyl chloride was added dropwise thereto; the mixture was heated while agitated at an internal temperature of 50 to 75° C. for 7 hours, and then cooled to 30° C. or lower. 420 ml of water was added thereto; the mixture was agitated for 5 minutes; and then the aqueous phase was removed. It was added to a mixture of 151.1 g of 2-amino-5-methybenzoic acid and 1200 ml of N,N-dimethylacetamide placed in a three-necked flask that was previously dissolved by agitation and agitated continuously as cooled in an ice-methanol bath, and the resulting mixture was stirred additionally for 2 hours. The internal temperature was 0 to 5° C. then. Then, 254 g of acetic anhydride and 300 ml of toluene were added thereto; the mixture was agitated and heated under solvent reflux for 1.5 hours and then cooled to 30° C. or lower; and the resulting crystal was filtered and dried, to give 194.2 g of a target exemplified compound (I-8) (yield: 98%). The content of sodium and potassium in the exemplified compound (I-8) obtained was 1 ppm or less.

<Evaluation>

(Preparation of Ultraviolet-Absorbing Filter)

150 ml of chloroform was added to 10 g of polymethyl methacrylate (PMMA) and 0.1 g of the compound represented by Formula (I) shown in Table 1, and the mixture was agitated and dissolved at 40° C. for 60 minutes; the resulting solution was coated on a glass plate and air-dried at room temperature, to give an ultraviolet-absorbing filter sample. As shown in Table 1, the compound represented by Formula (I) was prepared as a Comparative Example, according to the method described in Example 2 of U.S. Pat. No. 3,408,326 or the method described in Example 1 of JP-A-2000-264879.

(Light Fastness Test)

The sample obtained was exposed to the light from a xenon lamp at an intensity of 170,000 lux for 3 days, the intensities of the absorption at the maximum spectroscopic absorption wavelength of the compound represented by Formula (I) before and after irradiation were determined, and the light fastness was calculated based on the retention rate. Results are summarized in Table 1.

TABLE 1

| Sample No. | Exemplified Compound No. | Concentration of sodium in product | Light Fastness | Remarks | |
|---|---|---|---|---|---|
| 1 | (I-7) | 1 ppm or less | 98 | Isolated product of Example 1 of the present invention | This invention |
| 2 | (I-7) | 1 ppm or less | 99 | Isolated product of Example 2 of the present invention | This invention |
| 3 | (I-7) | 1 ppm or less | 98 | Isolated product of Example 3 of the present invention | This invention |
| 4 | (I-8) | 1 ppm or less | 98 | Isolated product of Example 4 of the present invention | This invention |
| 5 | (I-13) | 1 ppm or less | 97 | Isolated product of Example 5 of the present invention | This invention |
| 6 | (I-7) | 35 ppm | 88 | Prepared by the method of Example 2 of U.S. Pat. No. 3,408,326 | Comparative example |
| 7 | (I-7) | 360 ppm | 79 | Prepared by the method of Example 1 of JP-A-2000-264879 | Comparative example |
| 8 | (I-8) | 430 ppm | 85 | Prepared by the method of Example 1 of JP-A-2000-264879 | Comparative example |
| 9 | (I-13) | 460 ppm | 80 | Prepared by the method of Example 1 of JP-A-2000-264879 | Comparative example |

As obvious from the results shown in Table 1, the compounds represented by Formula (I) prepared by the method according to the present invention were higher in purity and light fastness than the compounds prepared by other preparative methods.

INDUSTRIAL APPLICABILITY

According to the present invention, a benzoxazinone-based compound useful as the ultraviolet absorbent for thermoplastic polymers can be produced inexpensively and effectively at high purity. The benzoxazinone-based compound produced by the present invention method can provide an ultraviolet absorbing material with high-purity and light fastness useful in optical film application.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-252729 filed in Japan on Sep. 27, 2007, and Patent Application No. 2008-091834 filed in Japan on Mar. 31, 2008, each of which is entirely herein incorporated by reference.

The invention claimed is:

1. A method of producing a compound represented by Formula (I), which comprises: a step A of allowing an anthranilic acid compound to react with a carboxylic halide in the absence of a base, but does not comprise any step of isolating an amide intermediate compound represented by Formula (II):

Formula (I)
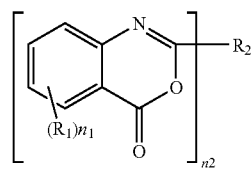

Formula (II)
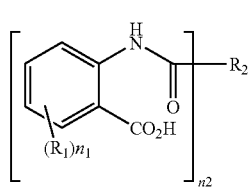

wherein $R_1$ represents a halogen atom, an alkyl group having 1 to 20 carbon atoms, an aryl group having 6 to 20 carbon atoms, an alkoxy group having 1 to 20 carbon atoms, an aryloxy group having 6 to 20 carbon atoms, an alkyl thio group having 1 to 20 carbon atoms or an aryl thio group having 6 to 20 carbon atoms; $n_1$ is an integer of 0 to 4; $R_2$ represents a bivalent or trivalent linking group selected from an alkyl group having 1 to 20 carbon atoms, an alkenyl group having 2 to 20 carbon atoms, an aryl group having 6 to 20 carbon atoms, a five- or six-membered heterocyclic group of N, O, or S and carbon atoms; and $n_2$ is an integer of 2 to 4, wherein the temperature of the step A is 50° C. or lower, and wherein at least one kind of a reaction solvent is used in the step A, and said at least one kind of a reaction solvent has a donor number of 10 or more.

2. The method according to claim 1, wherein no protic solvent is used in the step A.

3. The method according to claim 1, wherein the temperature of the step A is −15° C. or more and 20° C. or lower.

4. The method according to claim 1, wherein the carboxylic halide is prepared by acid halogenation of a carboxylic acid compound and used as it is without isolation after preparation.

5. The method according to claim 1, wherein $R_1$ represents a chlorine atom, a fluorine atom, an alkyl group having 1 to 4 carbon atoms or an alkoxy group having 1 to 4 carbon atoms and $R_2$ represents ethylene, trimethylene, 1,3-phenylene, 1,4-phenylene, pyrrole-2,5-yl, thiophene-2,5-yl, or benzene-1,3,5-yl.

6. The method according to claim 1, wherein said at least one kind of a reaction solvent has a donor number of 25 or more.

7. The method according to claim 6, wherein said at least one kind of a reaction solvent that has a donor number of 25 or more is N,N-dimethylformamide, N,N-dimethylacetamide, N-methylpyrrolidinone or hexamethylphosphoric triamide.

* * * * *